United States Patent [19]
Krivitski

[11] Patent Number: 6,155,984
[45] Date of Patent: Dec. 5, 2000

[54] METHOD AND APPARATUS FOR MEASURING CARDIAC OUTPUT THROUGH AN ARTERIAL CANNULA

[75] Inventor: Nikolai M. Krivitski, Ithaca, N.Y.

[73] Assignee: Transonic Systems, Inc., Ithaca, N.Y.

[21] Appl. No.: 09/293,117

[22] Filed: Apr. 15, 1999

[51] Int. Cl.[7] .................................................. A61B 5/026
[52] U.S. Cl. ........................................................ 600/526
[58] Field of Search ................................ 600/526, 528, 600/504–506, 547, 457, 454, 474, 478–480, 486

[56] References Cited

U.S. PATENT DOCUMENTS

| | | | |
|---|---|---|---|
| 5,046,505 | 9/1991 | Sekii et al. ............................... | 600/526 |
| 5,395,505 | 3/1995 | Band et al. ............................... | 204/418 |

*Primary Examiner*—Jeffrey R. Jastrzab
*Attorney, Agent, or Firm*—Brian B. Shaw, Esq.; Stephen B. Salai, Esq.; Harter, Secrest & Emery LLP

[57] ABSTRACT

The invention includes a dilution sensor for determining a blood property in a peripheral artery distal to the heart and lungs, wherein the dilution sensor may be exposed to the blood flow by passing through a pressure arterial catheter.

8 Claims, 2 Drawing Sheets

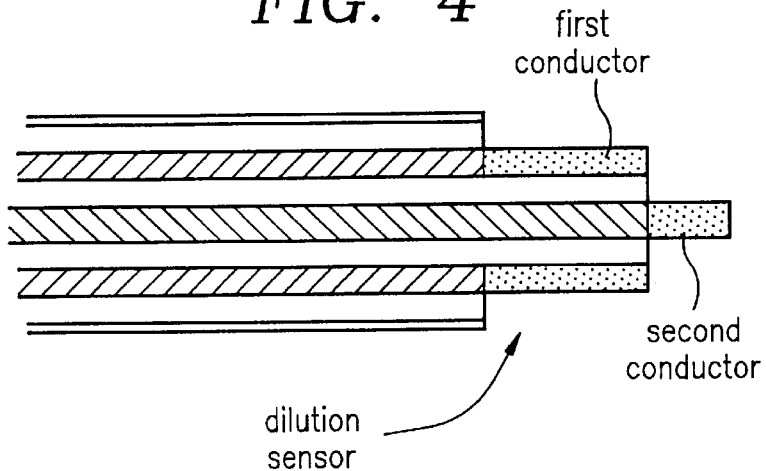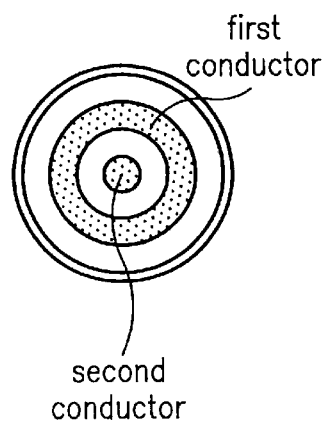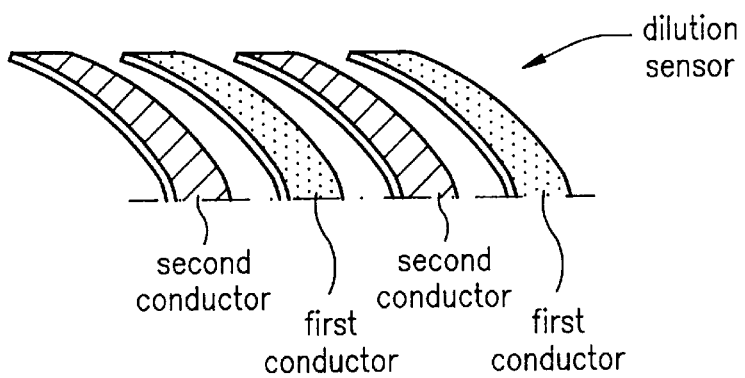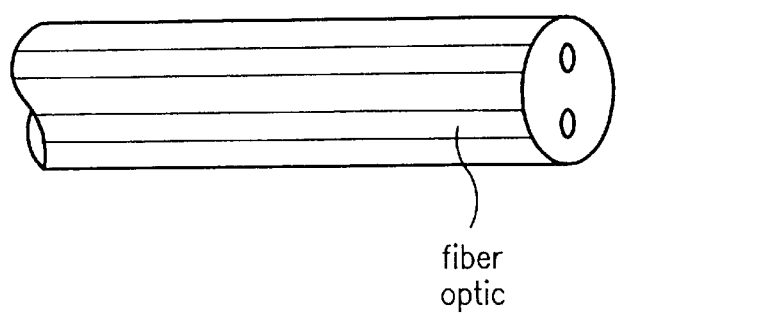

METHOD AND APPARATUS FOR MEASURING CARDIAC OUTPUT THROUGH AN ARTERIAL CANNULA

FIELD OF THE INVENTION

The present invention relates to monitoring cardiac parameters, and more particularly, to employing an arterial cannula distal to a central blood volume to determine cardiac output through the use of dilution technology. Specifically, the present invention provides for the calculation of cardiac output via a dilution sensor disposed in a arterial pressure cannula.

BACKGROUND OF THE INVENTION

Typically, pulmonary artery catheters (PAC) are used in the evaluation of hemodynamic parameters like cardiac output. However, the insertion, operation and removal of such catheters requires highly skilled personnel. These catheters are relatively large devices having a diameter of 3 to 5 mm. In addition, the PAC is inserted via a central vein into the pulmonary artery and thus has a length of approximately 1.2 m to 1.5 m.

Due to the size and location of the PAC, there are significant complications and risks associated with their use. For example, cardiac arrhythmia's, incorrect placement and vascular damage may occur during insertion of the PAC. Infection endocarditis, pulmonary artery aneurysm, or rupture or embolism of catheter fragments may occur during maintenance of the catheter location. Further, knotting or shredding of the catheter, cardiac arrhythmia's or further vascular damage may occur during removal of the catheter. The benefits of procedure must be carefully weighed against the risks. In addition, the PAC may be inappropriate for use in certain patients including children.

Therefore, a need exists for a method and apparatus for determining hemodynamic and cardiac parameters without requiring a cardiac or pulmonary catheter. A need also exits for a catheter that can be readily employed in a broad spectrum of patient without creating undue risks.

SUMMARY OF THE INVENTION

The present invention provides for the determination of cardiac output based on dilution technology from a sensor located distal to the heart and lungs.

More particularly, the present invention contemplates a dilution sensor sized to be introduced into a pressure arterial cannula. The dilution sensor may be operably located in the relevant vessel via a three-way stop cock in an arterial pressure cannula.

Generally, an indicator is injected intravenously to pass through the right heart, lungs and the left heart, and then travel to the peripheral artery sensor. An ultrasound velocity dilution, electrical impedance dilution sensor, optical sensor employing an isotonic saline as an indicator, may be employed to determine the cardiac output.

BRIEF DESCRIPTION OF THE DRAWINGS

FIG. 4 is a cross sectional view of a first configuration of an electrical impedance dilution sensor.

FIG. 5 is an end view of the electrical impedance dilution sensor of FIG. 4.

FIG. 6 is a cross sectional view of a second configuration of an electrical impedance dilution sensor.

FIG. 7 is a cross sectional view of a fiber optic dilution sensor.

DETAILED DESCRIPTION OF THE PREFERRED EMBODIMENT

Figure 1:
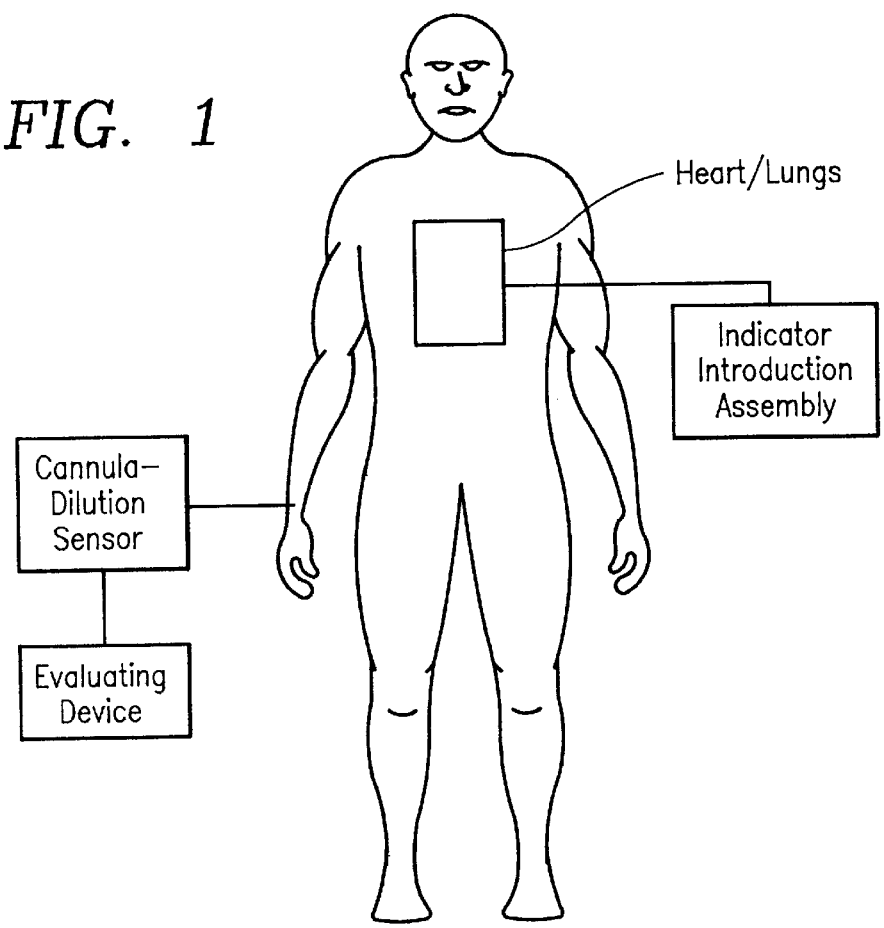
FIG. 1 is a schematic of an arterial pressure catheter with the present dilution sensor, indicator introduction assembly and evaluating device.
Figure 2:
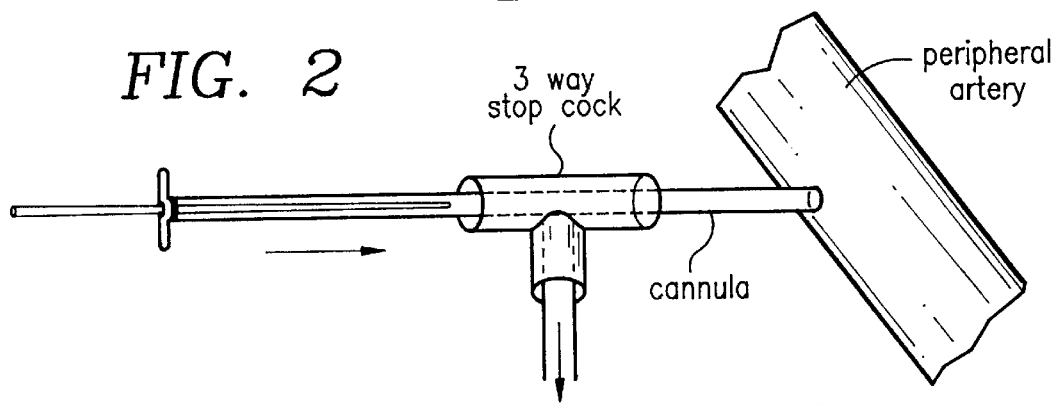
FIG. 2 is a schematic view of an arterial pressure catheter with a three-way stop cock.
Figure 3:
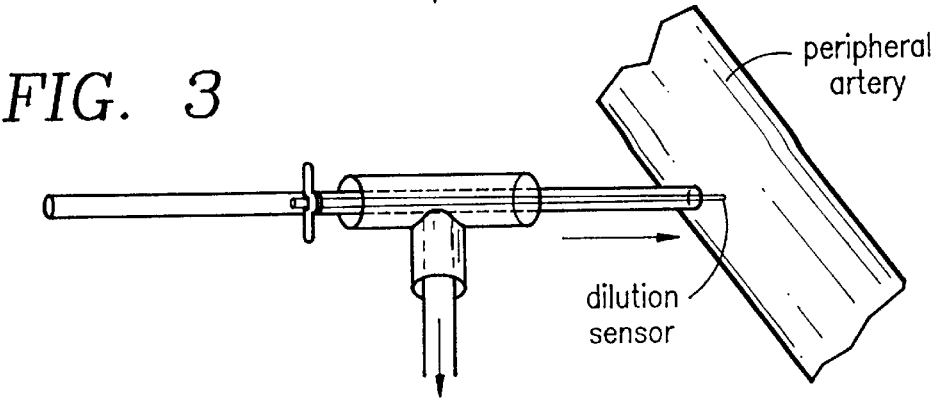
FIG. 3 is a schematic view of an arterial pressure catheter with a three-way stop cock and an impedance sensor being operably located in a vessel.

Referring to FIG. 1, the present invention includes a cannula, a dilution sensor, an indicator introduction assembly and an evaluating device. The present invention permits the use of an arterial cannula located in a relatively small peripheral artery to determine hemodynamic parameters including cardiac output. Unlike prior systems, the present invention determines hemodynamic parameters without requiring cardiac or pulmonary catheterization.

The present invention requires vascular penetration distal to the central blood volume. Preferably, the vascular access is obtained in the arm or hand of a patient. Thus, the insertion point is distal to the pulmonary and cardio portions of the circulatory system. The term "peripheral artery" is taken to be a vascular passage distal to the heart and lungs. It is understood the term peripheral artery includes the arm or hand of a patient.

The present invention is operable in a number of fluid regimes, for purposes of clarity and consistency, the present invention is set forth in a blood flow environment. The term "upstream" of a given position refers to a direction against the flow of blood, and the term "downstream" of a given position is the direction of blood flow away from the given position.

The "arterial" side or portion of the circulation system is that part in which oxygenated blood flows from the heart to the capillaries. The "venous" side or portion is that part in which blood flows from the capillaries to the heart and lungs.

The cannula is an arterial pressure cannula sized to be operably inserted into the peripheral artery in the arm or hand. Typically, the cannula has a diameter of approximately 1 mm and a length of approximately 5 cm to 7 cm.

A three way stop cock may be operably connected to the cannula. The stop cock includes valving for permitting selective fluid communication with the respective artery.

The dilution sensor is sized to be slideably received within the arterial cannula, and therefore, has a diameter less than the arterial cannula. Specifically, the dilution sensor diameter is less than approximately 1 mm. The dilution sensor has a sufficient length to locate a portion of the dilution sensor within the peripheral artery.

The dilution sensor is connected to the cannula to be moveable with respect to the cannula. In the moveable configuration, there are sliding seals between the dilution sensor and the cannula to permit the selective location of the dilution sensor, and more particularly, the sensor tip within the vessel. The seals are hermetic to preclude contamination or leakage to the peripheral artery through the cannula-dilution sensor interface. That is, the seals are configured to insure blood does not migrate along the cannula between the cannula and the dilution sensor.

The dilution sensor is configured to pass through the cannula to be located in the peripheral artery. The distal end of the dilution sensor is exposed to the blood flow in the peripheral artery, and provides a signal corresponding to at least one blood parameter. The dilution sensor includes leads extending from the arterial cannula to be connected to the evaluating device.

The dilution sensor may include one of a variety of sensors for determining a change in any physical or chemical blood parameter including thermal, optical, electrical, or a combination of parameters. Preferably, the dilution sensor is an impedance sensor or a sound velocity sensor. In the electrical impedance configuration, the dilution sensor is located at the distal end of the dilution sensor and has a coaxial configuration. As shown in FIG. 4, the coaxial dilution sensor includes a central conductor spaced from a concentric conductor. The relative position of the two conductors are further shown in FIG. 5.

Referring to FIG. 6, the electrical impedance dilution sensor may be alternatively configured as a pair of spaced insulated helixes. It is understood an ultrasound dilution sensor may be constructed as in FIGS. 4–6, wherein a sound generating terminal and a sound receiving terminal are spaced apart along the distal end of the dilution sensor.

As shown in FIG. 7, it is contemplated the dilution sensor may include optical fibers. The optical fibers extend the length of the dilution sensor to the distal end. The dilution sensor may include at least a pair of optical fibers. Specifically, one optical fiber projects an illuminating light into the blood flow and a second optical fiber transmits a resulting light intensity. That is, the blood property sensor includes a generating fiber optic and a recording fiber optic. Alternatively, a single fiber optic may be employed to generate and record light intensity.

In a specific configuration, it is contemplated that a three-way stop cock is operably connected to the arterial pressure cannula. The through line of the stop cock is aligned with the cannula and permits the dilution sensor to be slidably disposed there through.

The indicator introduction assembly includes a dilution indicator source and an introduction port. The introduction port is located on the venous side of the central blood volume and provides for the introduction of a dilution indicator. The indicator introduction port permits the controlled and monitored introduction of the dilution indicator into the blood stream to provide a dilution curve.

It is understood the indicator is any substance that alters a measurable blood property. The indicator may alter any measurable parameter of the blood. For example, the indicator may be chemical, optical, electrical, thermal or any combination thereof. The particular indicator is at least partially dictated by the anticipated operating environment. Available indicators include saline solutions, increased or decreased temperature as well as dyes and various isotopes. However, it is believed the use of temperature differentials is disfavored in the present application, as such differentials are significantly degraded upon passage through the central blood volume.

Evaluating Device

The evaluating device, controller, is operably connected to the dilution sensor, and preferably indicator introduction system to evaluate and compare corresponding dilution curves. The evaluating device may be any of a variety of digital or analog processors, as commonly found in desktop computers.

In addition, it is contemplated the evaluating device may control the operation of the dilution sensor. For example, the evaluating device may set the electrical signal through one of the conductors in the electrical impedance dilution sensor.

The evaluating device may also be selected to control the wavelength of the illuminating light in the optical fiber dilution sensor. However, it is understood the dilution sensor may be a separate component.

The ultrasound velocity in blood is primarily determined by the total blood protein concentration. The dilution indicator (for example isotonic saline) dilutes the blood and hence the blood protein concentration and a corresponding change in ultrasound velocity results.

For measuring cardiac output by ultrasound dilution, the following formula may be employed:

$$CO = V/S_v(V_b - V_o)$$

Where V is the volume of the isotonic saline injection [ml]; $V_b$ is the ultrasound velocity of blood flowing across the dilution sensor [m/sec]; $S_v$ is the area under the blood ultrasound velocity curve. It is understood that the dilution sensor must be calibrated to convert a recorded ultrasound velocity change into changes in the saline concentration in the blood.

Determination of cardiac output corresponding to electrical impedance dilution is based upon the electrical resistivity of blood. The electrical resistivity of blood is determined primarily by the hematocrit and the plasma ion concentration in the blood. An ejected isotonic saline dilutes blood, and thus, cardiac output can be calculated by:

$$CO = V \left( \frac{2 Z_b}{S_z} \right) \left( 1 + \sqrt{\frac{Z_b}{Z_i}} \right)$$

where V is the volume of the isotonic saline injection [ml]; $S_z$ is the area generated by changes in the blood electrical impedance curve [ohmXmin] and $Z_b$ and $Z_i$ are electrical impedance of the blood and the isotonic saline respectively [ohm]. It is understood that the dilution sensor must be calibrated to convert the changes in electrical impedance to changes in saline concentration and hence blood property concentration.

It is anticipated that isotonic saline boluses of approximately 3 to 30 ml produce a sufficient dilution curve.

Thus, the arterial cannula is located in a peripheral artery distal to the heart and lungs as shown in FIG. 1. The dilution sensor is then passed through the arterial cannula to locate the dilution sensor in the peripheral artery. The indicator is introduced in the circulation system of the patient and is recorded as it passes the calibrated dilution sensor. The evaluating device then determines the cardiac output in response to the recorded dilution curve from the dilution sensor.

While a preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed is:

1. A method of determining cardiac output comprising:
   (a) locating an arterial pressure cannula in a peripheral artery distal to the pulmonary artery and the aorta;
   (b) passing a dilution sensor through a portion of the arterial pressure cannula to locate the dilution sensor in the peripheral artery;
   (c) passing a dilution indicator through the right heart, the lungs and the left heart;

(d) detecting passage of the dilution indicator by the dilution sensor, distal to the pulmonary artery and the aorta; and (e) determining a cardiac output corresponding to passage of the dilution indicator by the dilution sensor.

2. The method of claim 1, further comprising removing the dilution sensor from the arterial pressure cannula.

3. The method of claim 1, further comprising passing the dilution sensor through a three way stop cock.

4. The method of claim 3, further comprising maintaining a hermetic seal between the arterial pressure cannula and the dilution sensor.

5. The method of claim 1, further comprising employing one of a change in a physical or chemical blood parameter as the dilution indicator.

6. The method of claim 1, wherein detecting passage of the dilution indicator includes detecting one of a thermal, optical, electrical or sound velocity parameter of the blood.

7. An apparatus for determining a cardiac output, comprising:

(a) an arterial pressure cannula;

(b) a three way stop cock connected to the arterial pressure cannula;

(c) a dilution sensor sized to be passed through a portion of the arterial pressure cannula and received in a peripheral artery distal to the heart and lungs to provide a signal in response to passage of a dilution indicator in the peripheral artery;

(d) a hermetic seal between the dilution sensor and one of the three way stop cock and the arterial pressure cannula; and (e) an evaluating device for determining a cardiac output corresponding to the signal from the dilution sensor.

8. An apparatus for determining a cardiac output, comprising:

(a) an arterial pressure cannula;

(b) a dilution sensor sized to be passed through a portion of the arterial pressure cannula and received in a peripheral artery distal to the heart and lungs to provide a signal in response to passage of a dilution indicator in the peripheral artery; and (c) an evaluating device for determining a cardiac output corresponding to the signal from the dilution sensor.

* * * * *